United States Patent
Zi et al.

(10) Patent No.: US 7,326,734 B2
(45) Date of Patent: Feb. 5, 2008

(54) TREATMENT OF BLADDER AND URINARY TRACT CANCERS

(75) Inventors: Xiolin Zi, Irvine, CA (US); Anne R. Simoneau, Long Beach, CA (US)

(73) Assignee: The Regents of the University of California, Oakland, CA (US)

( * ) Notice: Subject to any disclaimer, the term of this patent is extended or adjusted under 35 U.S.C. 154(b) by 32 days.

(21) Appl. No.: 10/817,449

(22) Filed: Apr. 1, 2004

(65) Prior Publication Data
US 2004/0259813 A1 Dec. 23, 2004

Related U.S. Application Data

(60) Provisional application No. 60/459,495, filed on Apr. 1, 2003.

(51) Int. Cl.
*A61K 31/121* (2006.01)
*A61K 31/352* (2006.01)

(52) U.S. Cl. .................... 514/685; 514/455
(58) Field of Classification Search ............ 514/685
See application file for complete search history.

(56) References Cited

U.S. PATENT DOCUMENTS

| | | | |
|---|---|---|---|
| 4,190,671 A | 2/1980 | Vanstone et al. | |
| 4,656,305 A | 4/1987 | Vanstone et al. | |
| 4,753,965 A | 6/1988 | Stemerick et al. | |
| 4,863,968 A | 9/1989 | Edwards et al. | |
| RE33,109 E | 11/1989 | Vanstone et al. | |
| 4,904,697 A | 2/1990 | Sunkara et al. | |
| 5,061,488 A | 10/1991 | Wiltrout et al. | |
| 5,068,364 A | 11/1991 | Takagaki et al. | |
| 5,089,654 A | 2/1992 | Yokomori et al. | |
| 5,126,129 A | 6/1992 | Wiltrout et al. | |
| 5,554,638 A | 9/1996 | Dewhirst et al. | |
| 5,612,310 A | 3/1997 | Dewhirst et al. | |
| 5,703,130 A | 12/1997 | Han et al. | |
| 6,046,212 A | 4/2000 | Zwaagstra et al. | |
| 6,286,513 B1 * | 9/2001 | Au et al. ............ | 128/898 |
| 6,297,274 B1 | 10/2001 | Cheng et al. | |
| 6,462,075 B1 | 10/2002 | Bowen et al. | |
| 6,524,625 B2 | 2/2003 | Aga et al. | |
| 6,576,660 B1 | 6/2003 | Liao et al. | |
| 6,624,138 B1 | 9/2003 | Sung et al. | |
| 6,737,439 B2 | 5/2004 | Kinghorn et al. | |
| 6,906,105 B2 | 6/2005 | Bowen et al. | |
| 6,984,667 B2 | 1/2006 | Theoharides | |

FOREIGN PATENT DOCUMENTS

WO    WO03/106384    * 12/2003

OTHER PUBLICATIONS

U.S. Appl. No. 10/072,823, filed Feb. 2003, Sophie Chen.*
Gerhauser, C. et al., "Cancer Chemopreventative activity of Xanthohumol, a Natural Product Derived from Hop," Molecular Cancer Therapeutics, (2002).*
Miranda et al., *Prenylated chalcones and flavanones as inducers of quinine reductase in mouse Hepa 1c1c7 cells*, Cancer Letters 2000, vol. 149, pp. 21-29.
Ha et al., *Prenylated Flavonoids from the Heartwood of Artocarpus communis with Inhibitory Activity on Lipopolysaccharide-Induced Nitric Oxide Production*, J. Nat. Prod. 2006, vol. 69, pp. 719-721.
Zi et al., *Flavokawain A, a Novel Compound from Kava Extract, could be used for Bladder Cancer Prevention and Intervention*, presentation slides, University of California, Irvine, Dec. 2, 2002.
ACCR Abstract #104826, Nov. 1, 2002.

* cited by examiner

*Primary Examiner*—Shaojia Anna Jiang
*Assistant Examiner*—Eric S Olson
(74) *Attorney, Agent, or Firm*—Robert D. Buyan; Stout, Uxa, Buyan & Mullins, L.L.P.

(57) ABSTRACT

Compositions of matter and methods wherein chalcone and flavone derivatives are administered to human or veterinary patients for the treatment of bladder or urinary tract cancer. Compounds of the invention include 2'-hydroxy-4,4',6'-trimethoxychalcone (Flavokawain A).

8 Claims, 5 Drawing Sheets

TREATMENT OF BLADDER AND URINARY TRACT CANCERS

RELATED APPLICATION

This patent application claims priority ro U.S. Provisional Patent Application No. 60/459,495 entitled Treatment of Bladder and Urinary Tract Cancers Using Chalcome and Flavone Derivatives, which was filed on Apr. 1, 2003, the entirety of which is expressly incorporated herein by reference.

FIELD OF THE INVENTION

The present invention relates generally to biology and medicine, and more particularly to compositions and methods for treating bladder and urinary tract cancers.

BACKGROUND OF THE INVENTION

New therapies and improved diagnoses of bladder cancer have significantly lowered the number of deaths from the disease. However, bladder cancer remains a significant cause of morbidity and mortality in the United States and many other countries.

Smoking is a significant risk factor for bladder cancer because many of the cancer-causing chemicals in tobacco smoke are absorbed by the lungs, filtered by the kidneys, and excreted into the urine. When the urine is stored in the bladder, these chemicals can then damage the cells lining the bladder. The most common symptom of bladder cancer is blood in the urine.

There are three main types of bladder cancer:
i) Urothelian Carcinoma. Also called transitional cell carcinoma, this is the most common type of bladder cancer, occurring in 90 percent of all cases.
These cancers are usually superficial (75 percent of the time) and haven't gone very far into the bladder;
ii) Squamous Cell Carcinoma. Accounts for three to eight percent of bladder cancers, and is likely to have invaded farther into the bladder than urothelian carcinoma; and
iii) Adenocarcinoma. Also likely to involve deeper layers of the bladder; accounts for a small fraction of bladder cancers.

In cases of bladder cancer, cancer cells invade the wall of the bladder. The wall of the bladder consists of several layers and the treatment modalities used to treat bladder cancer are typically selected on the basis of how far the cancer has penetrated into the layers of the bladder wall.

The majority of superficial tumors (e.g., those that are confined to the mucosa and lamina propria of the bladder) are treated by urologists by way of cystoscopic surgery and in select cases intravesical drug therapy. Although these superficial bladder cancers frequently recur and may be multifocal, the survival rates following treatment are generally excellent. However, in cases where the carcinoma has penetrated the muscular wall of the bladder (i.e. where the cancer has progressed to invasive bladder cancer that invades the deeper layers of the bladder wall, and possibly nearby organs, such as the uterus, vagina, or prostate gland) the prognosis is typically worse. Approximately 50% of patients with muscle-invasive bladder cancer will develop metastatic disease. For this reason, there is a clear need for effective systemic therapy for bladder cancer.

A variety of single agents have significant activity in transitional cell carcinoma of the bladder. Cisplatin-based regimens such as MVAC (methotrexate, vinblastine, doxorubicin, and cisplatin) have become standard for patients with metastatic urothelial carcinoma. The response rate to this combination therapy developed almost 20 years ago has been found to be as high as 72% with a 36% complete response rate (Stemberg, C. N. et al; Cancer 1989, 64, 2448). The median survival of patients with metastatic bladder cancer treated with M-VAC is approximately 1 year and long-term survival occurs in a small proportion of patients. Randomized trials have demonstrated that MVAC is superior to single-agent cisplatin and to CISCA (cyclophosphamide, doxorubicin, and cisplatin) (Loehrer, P. J. et.al., J. Clin. Oncol. 1992, 10, 1066 and Logothetis, C. J. et.al., J. Clin. Oncol. 1990, 8, 1050). However, the drawback of MVAC is toxicity and poor patient tolerance. In clinical trials, the combination had substantially more toxicity including mucositis, myelosuppression, and treatment-related deaths than did single-agent cisplatin. Additionally, patients with advanced urothelial carcinoma may have age- and/or disease-related abnormalities in renal function making the utilization of a cisplatin-based regimen problematic. Nonetheless, MVAC remains an important landmark in the development of chemotherapy in bladder cancer.

Further attempts to improve results with MVAC have focused on circumventing toxicity and intensifying dose. The utilization of the hematopoietic growth factor granulocyte-colony stimulating factor (G-CSF) has shown reduction in some of the toxicities, including decreased number of days of significant granulocytopenia, the need for antibiotics for granulocytopenic fever, and the incidence and severity of mucositis, associated with the MVAC regimen. However, dose intensification of MVAC utilizing hematopoietic growth factors has been attempted in several studies, with generally disappointing results (Seidman, A. D. et.al., J. Clin. Oncol. 1993, 11, 408 and Logothetis, C. J. et.al., J. Clin. Oncol. 1995,13, 2272).

Thus, MVAC is an active but toxic regimen for advanced bladder cancer. Given the small chance for long-term survival for most patients treated with this regimen, efforts to identify new agents and combinations with improved efficacy or tolerability have been ongoing.

New agents with significant activity include the taxanes paclitaxel and docetaxel, gemcitabine, ifosfamide, and the methotrexate analogues, trimetrexate and piritrexim. A large number of phase I-II trials have evaluated these agents in two- and three-drug combination regimens Paclitaxel demonstrated significant activity against human bladder cancer cell lines and in Phase II trial, paclitaxel with prophylactic G-CSF in patients with previously untreated advanced transitional cell carcinoma of the urothelium demonstrated an objective response (response rate of 42%). Toxicities included granulocytopenia, anemia, mucositis, and neuropathy. This study demonstrated that paclitaxel is among the most active single agents in this disease site (Roth, B. J. et. al., J. Clin. Oncol. 1994, 12, 2264). Based on this initial trial, paclitaxel-based regimens have been developed including doublet and triplet combinations with carboplatin, cisplatin, gemcitabine, ifosfamide, methotrexate, and other agents.

Gemcitabine is a deoxycitidine antimetabolite with a structure similar to cytarabine and has been approved for the palliative treatment of patients with advanced pancreas cancer. Gemcitabine has broad antitumor activity, including in bladder cancer. Response rates in the clinical trials were less than 30% and median survival was less than 12 months. In all these phase II trials, toxicity was in general mild and reversible. Combination of gemcitabine and cisplatin showed a better response rate (41%) but toxicity included grade 3-4 granulocytopenia and thrombocytopenia.

A better understanding of the molecular biology of bladder cancer will undoubtedly influence the selection of new therapeutic modalities. Molecular targeted small molecule therapy and monoclonal antibodies have begun to dominate contemporary studies. Whether or not this approach to therapy will lead to better results must still be determined in clinical trials.

Although only 20% of bladder cancers are clinically advanced at presentation, up to one-half of patients with infiltrating disease will recur or develop metastases and will die. On the basis of the relatively high response rate obtained with combination chemotherapy in patients with advanced or metastatic transitional cell carcinoma, urothelial cancer can be considered a chemosensitive disease. Nevertheless, long-term survival remains low and chemotherapy may provide the potential for cure only in selected patients.

Although several active combinations incorporating new agents, such as Gemcitabine and paclitaxel, have been evaluated in recent years, there are, at the moment, no clear-cut data demonstrating that these regimens are able to improve patient survival or to prolong response duration.

Chalcones and flavones are abundantly present in nature from ferns to higher plants. Chalcones are aromatic compounds and exhibit the basic structure with two benzene rings linked through an α,β-unsaturated carbonyl group (Formula 1). The flavones are phenylbenzo-pyrones (phenylchromones) with an assortment of structures based on a common three-ring nucleus. The basic flavone structure is comprised of two benzene rings (A and B) linked through a heterocyclic pyrone ring in the middle (Formula 2).

Chalcones have been reported to be anti-inflammatory, analgesic and antipyretic, whereas flavones show many pharmacological properties. Some chalcones possess bactericidal, antifungal and insecticidal activity and some of their derivatives are reported to be antimutagenic. *Piper methysticum* Forst. f. (Kava Kava) belongs to the family Piperaceae, and grows as a perennial shrub in Fiji and other South Pacific islands, where its root extract has been traditionally used as a beverage for thousands of years in social, recreational and ceremonial events, and also as a remedy for stress and anxiety. Due to its beneficial health effects, *P. methysticum* has gained popularity recently in western countries as an alternative medicine especially for the treatment of anxiety disorders. The chemistry of *P. methysticum* has been extensively studied, and SO far more than 40 compounds belonging to the classes of kavapyrones, alkaloids, steroids, chalcones, long-chained fatty acids and alcohols have been isolated and identified. Among these compounds, kavalactones have been recognized as the constituents responsible for the reported biological activities in Kava. Eighteen different kavalactones have been reported from the root extracts of Kava and desmethoxyyangonin, yangonin, dihydrokawain, kawain, dihydromethysticin and methysticin are the most abundant. Three chalcones, Flavokawains A, B and C were also isolated and synthesis of these have been previously reported (Dutta et. al., 1978. J. Indian Chem. Soc., 55, 932 and references cited therein; He et. al. 1997. Planta Medica, 63, 70; Ranjith et. al. 2002. Phytochemistry, 59, 429. Also see, Ono et. al. U.S. Pat. No. 6,303,157, issued Oct. 16, 2001 and McCleary et. al. PCT Int. Appl. 2002 WO 0291966). Wu et. al. (J. Agric. Food Chem. 2002, 50, 701) have shown that root extract demonstrates good to moderate inhibition against cyclooxygenase (COX) enzymes. The extract from above-ground growing parts of *Piper methysticum* Forst, especially leaves, shows a different chemical and pharmacological profile (Bueter, PCT Int. Appl. 2002 WO 0207743).

However, there are only scanty reports on the activity of chalcones against cancer. Anto et.al. (Cancer Letters 1995, 97, 33) investigated synthetic chalcones for their cytotoxic and tumor reducing activities. Methyl and hydroxy substituted chalcones were found to be cytotoxic in vitro whereas only hydroxy substituted chalcones could reduce ascites tumor in animals. However, anticancer activity of chalcone derivatives of this invention has not been reported. On the other hand, a study by Reina et. al. (Nutrition and Cancer 1999, 35, 212) did not find any relationship of bladder cancer occurrence and dietary intake of carotenoids (α-carotene, β-carotene, lutein and lycopene) and flavonoids (quercetin, kaempferol, myricetin and luteolin) and concluded that the study did not support the hypothesis that these specific carotenoids and flavonoids are protective against bladder cancer. It is most likely that the amount of flavones derivatives of this invention were not adequate to exert a pharmacological effect.

SUMMARY OF THE INVENTION

The present invention provides methods for treating (i.e., preventing the occurrence of, or treating after the occurrence of, the cancer) bladder and urinary tract cancers in human or veterinary patients. The methods of the present invention generally comprise the step of administering to the patient a therapeutically effective amount of one or more of the compounds, such as substituted chalcone and flavone derivatives, of formulae 1, 2, 3A, 3B, 3C and 4A and 4B as set forth below:

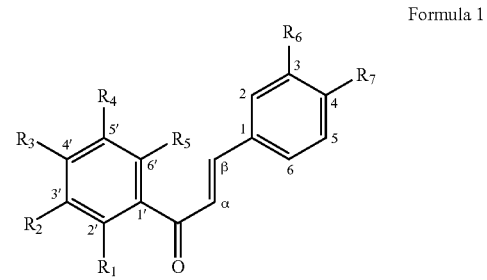

Formula 1

Wherein;

$R_1$, $R_3$, $R_5$, $R_6$ and $R_7$ are selected from H, OH, O-Alkyl, O-Alkenyl, O-Acyl; O-Glucosyl, O-Sulphate, )-Glucoronate and O-Amino Acid, halogen, amino, substituted amino and oxygen atom;

$R_2$ and $R_4$ are selected from H, alkyl and alkenyl, wherein the said alkyl and alkenyl groups have from 1 to 10 carbon atoms and up to 4 double bonds; and the hydrogen on the α-carbon of the olefinic double bond may or may not be substituted with a methyl, phenyl or substituted phenyl group.

In some cases, where the R5 of Formula 1 is an oxygen atom, the oxygen atom of R5 may connect to the β-carbon atom of the olefinic double bond to form a flavone derivative of Formula 2, as follows:

Formula 2

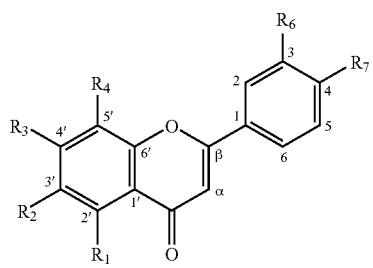

In some cases, where the $R_2$ of Formula 1 above is alkenyl, such as prenyl, and $R_3$ is OH, those $R_2$ and $R_3$ substituents may combine to form a cyclic ring structure as in Formula 3A:

Formula 3A

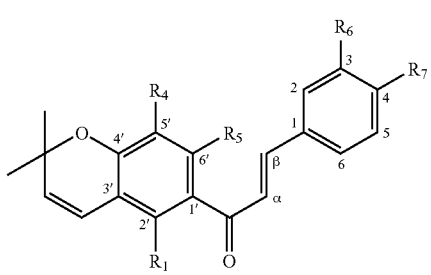

In some cases, where the $R_4$ of Formula 1 above is alkenyl, such as prenyl, and $R_3$ is OH, those $R_3$ and $R_4$ substituents may combine to form a cyclic ring structure represented by Formula 3B.

Formula 3B

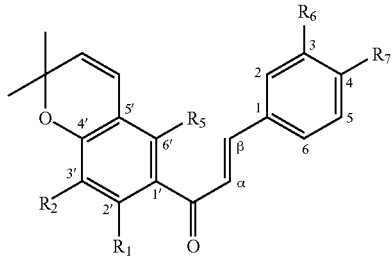

In some cases, where the $R_4$ of Formula 1 above is alkenyl, such as prenyl, and the $R_5$ is OH, such $R_4$ and $R_5$ substituents may combine to form ta cyclic ring structure as shown in the following Formula 3C.

Formula 3C

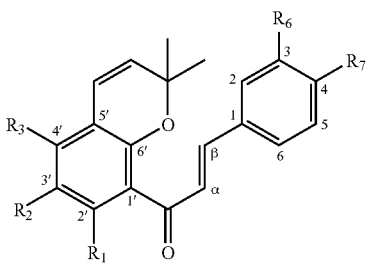

In some cases, when the $R_2$ of Formula 2 above is alkenyl, such as prenyl, and $R_3$ is OH, such $R_4$ and $R_5$ substituents may combine to form a cyclic ring structure of the following Formula 4A.

Formula 4A

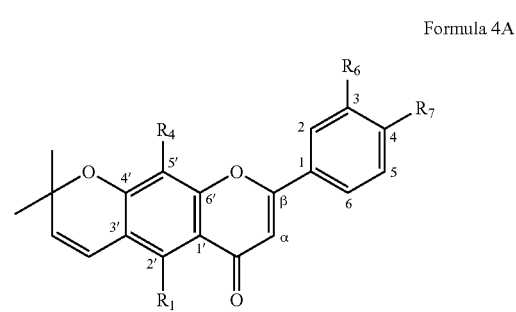

In some cases, where the $R_4$ of formula 2 above is alkenyl, such as prenyl, and $R_3$ is OH, such $R_3$ and $R_4$ substituents may combine to form a cyclic ring structure of the following Formula 4B.

Formula 4B

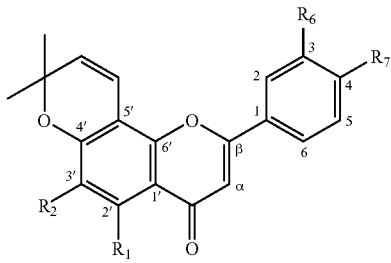

DETAILED DESCRIPTION AND EXAMPLES

Figure 1:
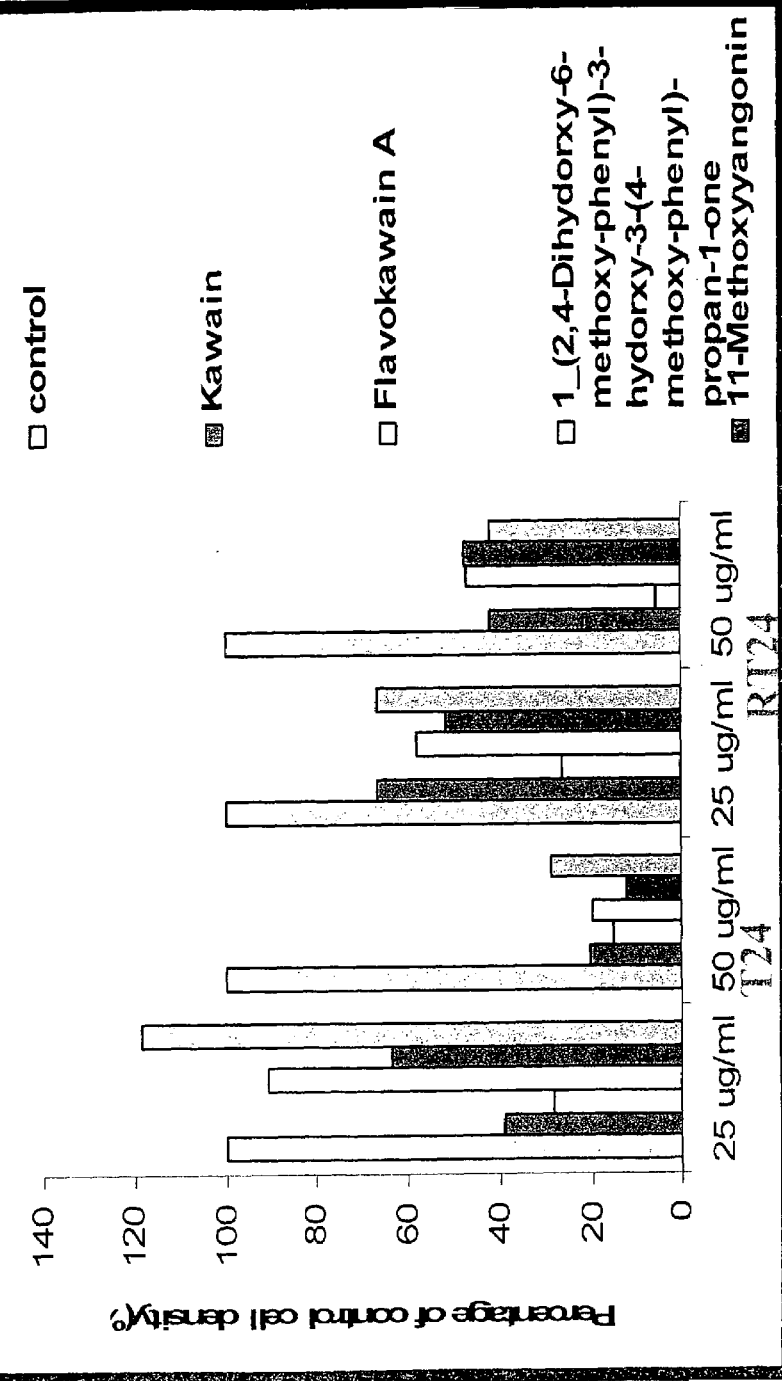
FIGS. 1-4 are graphs showing the effects of certain compounds of the present invention of the growth of bladder cancer cells in vitro.
Figure 2:
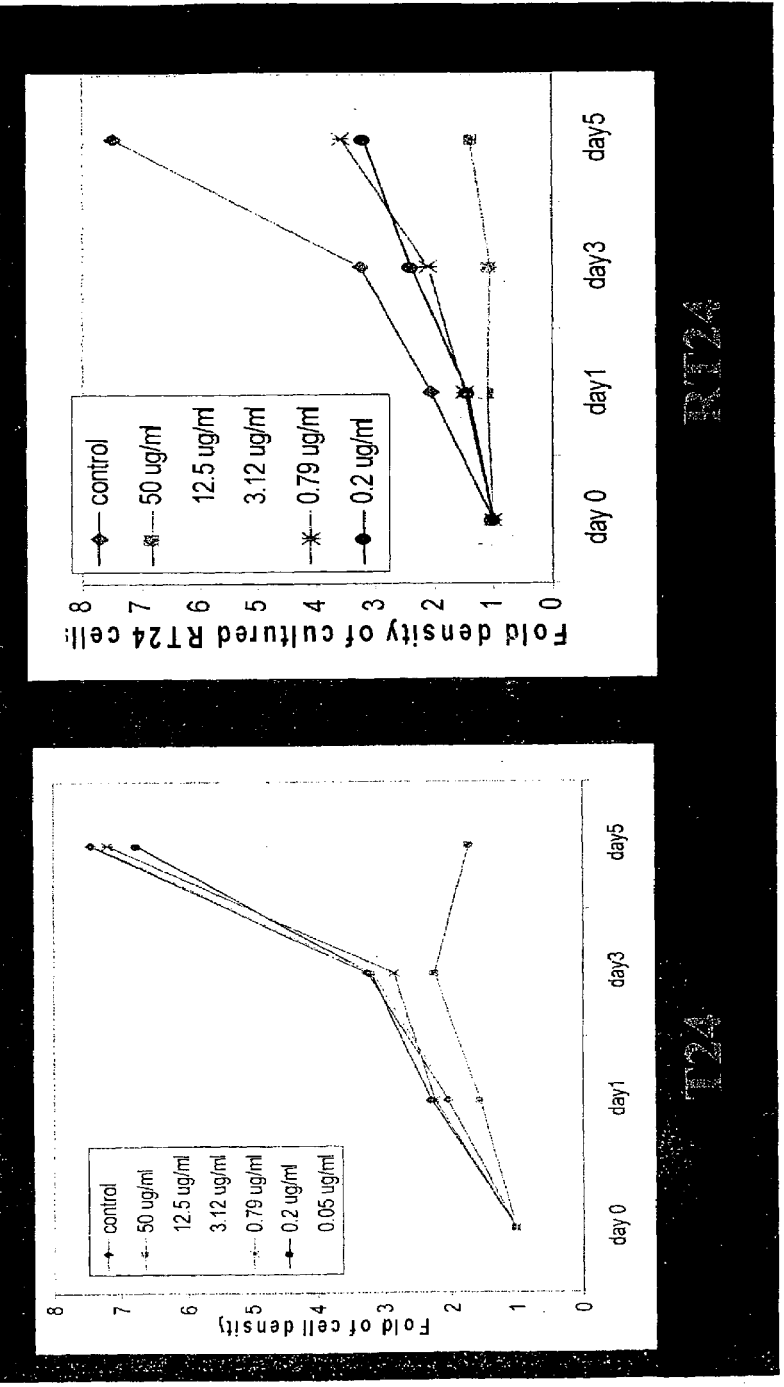
Figure 3:
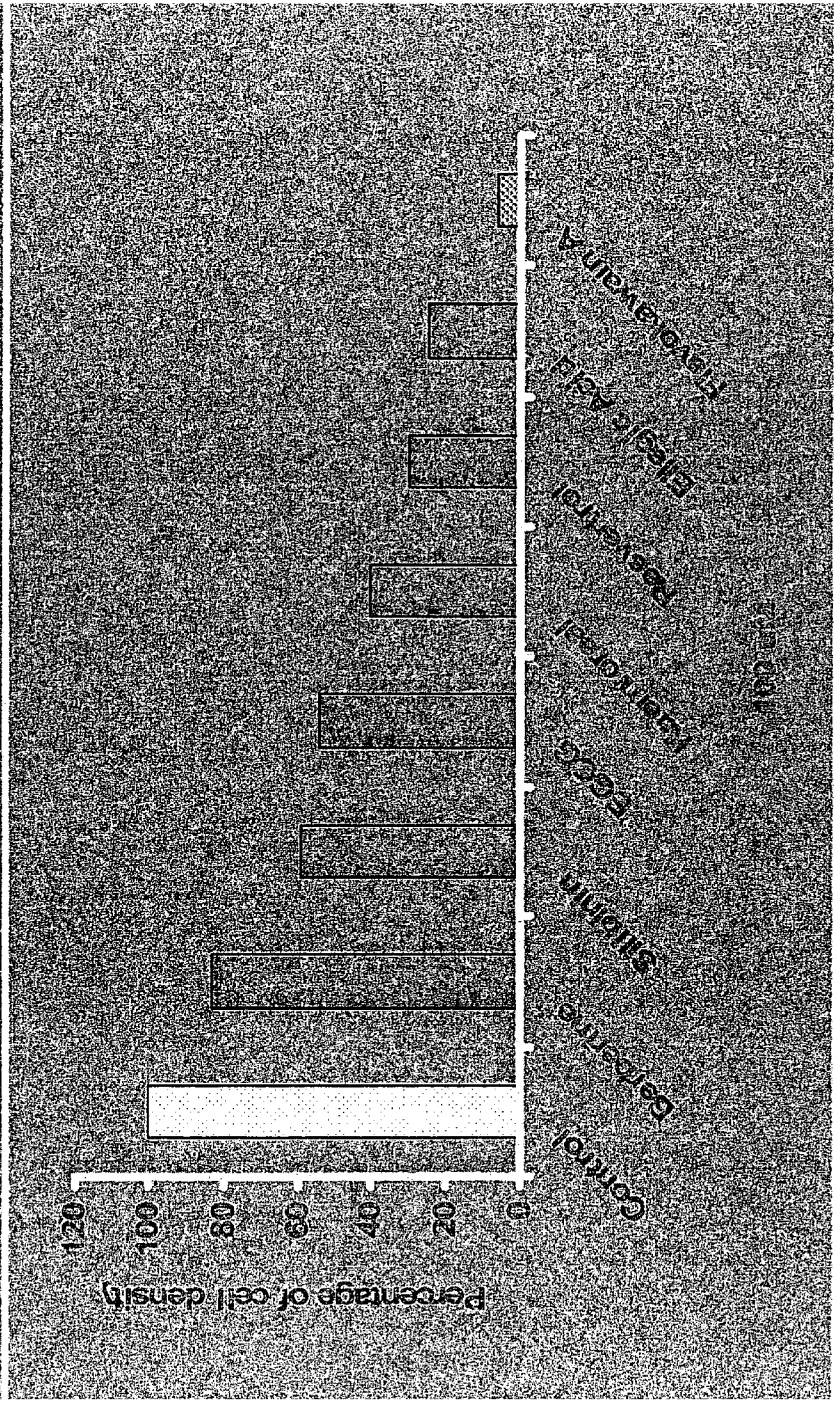
Figure 4:
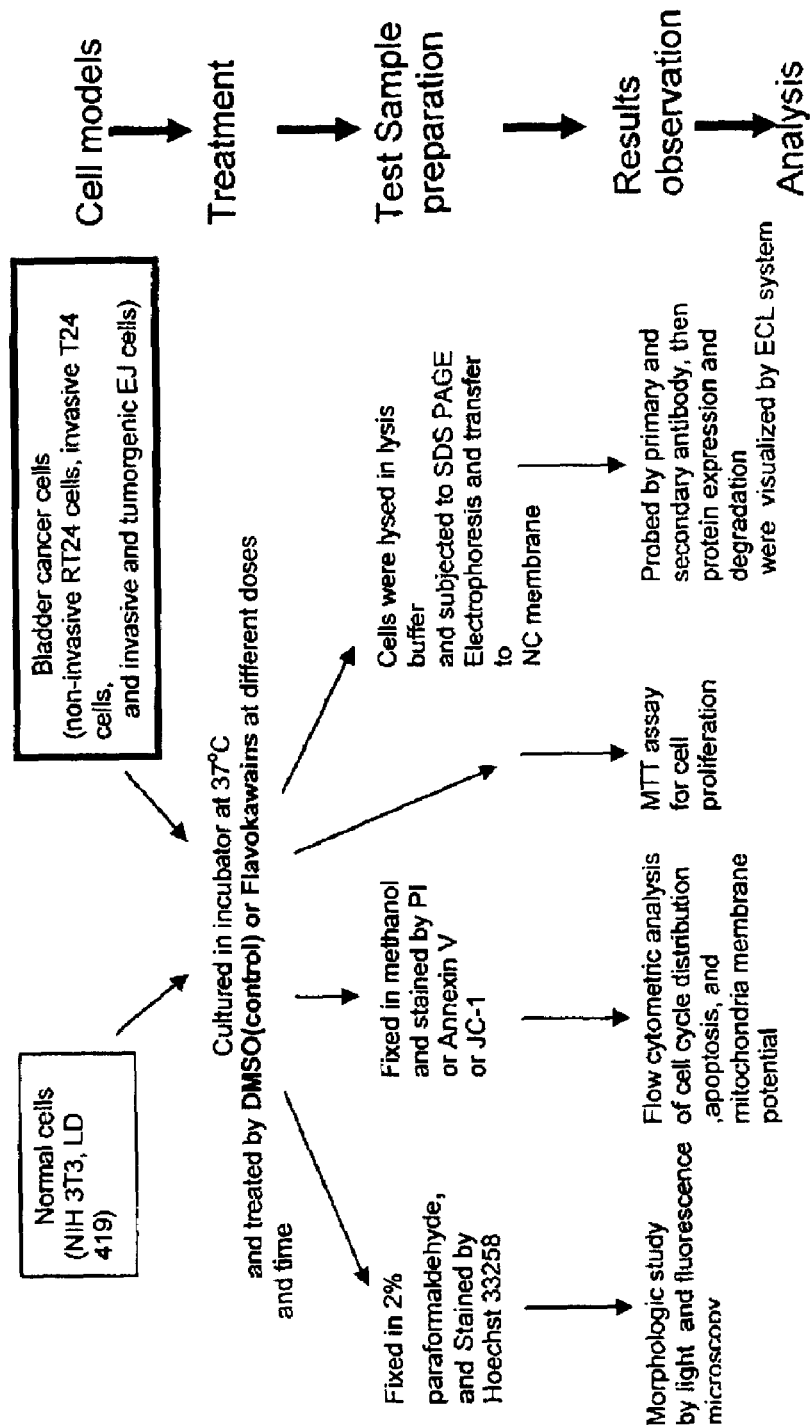

The chalcone and flavone derivatives of this invention are useful for the treatment of bladder or urinary tract cancer and are non-toxic as compared to the currently approved and investigational therapeutic agents. The latter, although effective, exhibit high toxicity. The compounds of this inventions are also strong antioxidants and can be used in combination with one or more of agents selected from cisplatin, carboplatin, paclitaxel, docetaxel, gemcitabine, ifosfamide, and the methotrexate analogues, trimetrexate and piritrexim.

In accordance with the invention, there is provided a method for treating bladder or urinary tract cancer in a mammalian patient by administering to the patient a therapeutically effective amount of at least one compound having the general structural Formula 1, 2, 3A, 3B, 3C and 4A or 4b, as set forth above.

In certain embodiments of Formula 1, the $R_1$, $R_3$, $R_5$, $R_6$ and $R_7$ are selected from H, OH, O-methyl, O-prenyl, O-geranyl, O-Acetyl; O-Glucosyl, O-Sulphate, -Glucoronate and O-Amino Acid, halogen, amino and substituted amino and the $R_2$ and $R_4$ are selected from H and Alkenyl; preferably Prenyl. For example, Formula 1 includes the following specific compounds:
  i) 4'-hydroxy-4,2',6'-trimethoxychalcone
  ii) 4,4'-dihydroxy-2',6'-dimethoxychalcone
  iii) 4',6'-dihydroxy-2',4-dimethoxychalcone
  iv) 2'-hydroxy-4,4',6'-trimethoxychalcone (Flavokawain A)
  v) 2'-4-dihydroxy-4',6'-dimethoxychalcone (Flavokawain C)
  vi) 2',4,4',6'-tetrahydroxychalcone (Chalconaringenin)
  vii) 2',4,6'-trihydroxy-4'-methoxy-3'-prenylchalcone (Xanthogalenol)
  viii) 2',4,4',6'-tetrahydroxy-3'-prenylchalcone (Desmethylxanthohumol)
  ix) 2',4,4',6'-tetrahydroxy-3'-geranylchalcone
  x) 2',4,6'-trihydroxy-4-methoxy-3',5'-diprenylchalcone
  xi) 2',4-dihydroxy-6'-methoxy-4'-prenyloxy-3',5'-diprenylchalcone
  xii) 2',4',3,4-tetrahydroxychalcone (Butein)
  xiii) 4,2',4'-trihydroxy-6'methoxychalcone 4'-glucoside (Gnaphalin)
  xiv) 2',6',4-trimethoxy-4'-hydroxy-3'-prenylchalcone In certain embodiments of Formula 2 above, the $R_1$, $R_3$, $R_6$ and $R_7$ are selected from H, OH, O-methyl, O-prenyl, O-geranyl, O-Acetyl; O-Glucosyl, amino and substituted amino and $R_2$ and $R_4$ are selected from H and alkenyl, most preferably, prenyl and geranyl. For example, Formula 2 includes the following specific compounds:
  i) 5,7,3',4'-tetrahydroxyflavone (Luteolin)
  ii) 5,7,4'-trihydroxyflavone (Apigenin)
  iii) 5,7,4'-trihydroxy-6-geranylflavone
  iv) 5,7,4'-trihydroxy-6,8-prenylflavone
  v) 5,7,4'-trihydroxy-6-prenylflavone
  vi) 7,4'-dihydroxy-5-methoxy-6-prenylflavone
  vii) 7,4'-dihydroxy-5-methoxy-8-prenylflavone
  viii) 5,7,3',4'-tetrahydroxy-6-prenylflavone
  ix) 5,7,3',4'-tetrahydroxy-8-prenylflavone
  x) 5,3',4'-trihydroxy-7-prenyloxyflavone In certain embodiments of Formula 3A above, the $R_1$, $R_4$, $R_5$, $R_6$ and $R_7$ are selected from H, OH, O-methyl and O-glucosyl. For example, Formula 3A includes the following specific compounds:
  i) 2',6',4-trihydroxy-3',4'-dehydrocyclohexanochalcone
  ii) 2',4-dihydroxy-6-methoxy-3',4'-dehydrocyclohexanochalcone
  iii) 2',3,4-trihydroxy-3',4'-dehydrocyclohexanochalcone
  iv) 2',4,6'-trihydroxy-3',4'-dehydrocyclohexanochalcone
  v) 2',6'-dimethoxy-4-hydroxy-3',4'-dehydrocyclohexanochalcone In certain embodiments of Formula 3B above, the $R_1$, $R_2$, $R_5$, $R_6$ and $R_7$ are selected from H, OH, O-methyl and O-glucosyl. For example, Formula 3B includes the following specific compounds:
  i) 2',6'dimethoxy-4-hydroxy-4',5'-dehydrocyclohexanochalcone
  ii) 2',3'-dihydroxy-6',4-dimethoxy-4',5'-dehydrocyclohexanochalcone
  iii) 2',6',3,4-tetrahydroxy-4',5'-dehydrocyclohexanochalcone
  iv) 2',6'-dimethoxy-3,4-dihydroxy-4',5'-dehydrocyclohexanochalcone In certain embodiments of Formula 3C above, the $R_1$, $R_2$, $R_3$, $R_6$ and $R_7$ are selected from H, OH, O-methyl and O-glucosyl. For example, Formula 3C includes the following specific compounds:
  i) 4'-hydroxy-2',4-dihydroxy-5',6'-dehydrocyclohexanochalcone
  ii) 2',4',4-trihydroxy-5',6'-dehydrocyclohexanochalcone
  iii) 2',4'-dihydroxy-4-methoxy-5',6'-dehydrocyclohexanochalcone
  iv) 2',4-dimethoxy-4'-hydroxy-5',6'-dehydrocyclohexanochalcone In certain embodiments of Formula 4A above, the $R_1$, $R_4$, $R_6$ and $R_7$ are selected from H, OH, O-methyl and O-glucosyl. For example, Formula 4A includes the following specific compounds:
  i) 5,3',4'-trihydroxy-6,7-dehydrocyclohexanoflavone
  ii) 5,4'-dihydroxy-6,7-dehydrocyclohexanoflavone
  iii) 5-hydroxy-4'-hydroxy-6,7-dehydrocyclohexanoflavone 4'-glucoside In certain embodiments of Formula 4B above, $R_1$, $R_2$, $R_6$ and $R_7$ are selected from H, OH, O-methyl and O-glucosyl. For example, Formula 4B includes the following specific compounds:
  i) 5,3',4'-trihydroxy-7,8-dehydrocyclohexanoflavone
  iv) 5,4'-dihydroxy-7,8-dehydrocyclohexanoflavone
  ii) 5-hydroxy-4'-hydroxy-7,8-dehydrocyclohexanoflavone 4'-glucoside The synthetic pathway for the preparation of chalcones and flavones are well established in the literature and known to one of ordinary skill in the art. For example, the chalcones are generally prepared by reacting a substituted acetophenone with a substituted benzaldehyde in presence of a catalyst, preferably a base, by Claisen-Scmidt Reaction (For example, Dutta et.al., J. Indian Chem. Soc. 1978, 55, 932 and 1976, 53, 1194). Synthesis of flavones is described in Harborne et al., 1975 The Flavonoids, Academic Press, New York; Harborne and Mabry, 1982 The Flavonoids: Advances in research. Chapman and Hall 1982; J. B. Harborne, The Flavonoids: Advances in Research since 1980, Chapman and Hall, 1988 and Vivian Cody, Elliott Middleton, Jr., Jeffrey B. Harborne, Plant flavonoids in biology and medicine: biochemical, pharmacological, and structure activity relationships: proceedings of a symposium held in Buffalo, N.Y., Jul. 22-26, 1985, New York: Liss, 1986 and references cited therein, all of which are hereby incorporated by reference.

The term "effective amount" means an amount of at least one compound of formula 1, 2, 3A, 3B, 3C, 4A and or 4B, or a pharmaceutically acceptable salt of such compound, that is effective to treat (e.g., prevent the occurrence or treat after the occurrence of) bladder or urinary tract cancer. The specific dose of compound administered according to this invention to obtain therapeutic or abrogatory effects will, of course, be determined by the particular circumstances surrounding the case, including, for example, the compound administered, the route of administration, the condition being treated and the individual host or patient being treated. An exemplary daily dose (administered in single or divided doses) contains a dosage level of from about 0.01 mg/kg to about 100 mg/kg of body weight of a compound of this invention. Preferred daily doses generally are from about 0.05 mg/kg to about 50 mg/kg and, more preferably, from about 0.1 mg/kg to about 25 mg/kg. Furthermore, the compounds of this invention, with their strong antioxidant action and bladder cancer inhibitory potential, cisplatin, carboplatin, taxanes such as paclitaxel and docetaxel, gemcitabine, ifosfamide, methotrexate and its analogues such as trimetrexate and piritrexim, thiotepa, doxorubicin (Adriamvcin®, Pharmacia & Upjohn, Kalamazoo, Mich.) mitomycin may be used additively or synergistically with current therapeutic agents, including and most commonly used combination therapies used to prevent recurrence and progression, particularly of superficial tumors (75% of all bladder cancers).

The compounds of the invention may be administered by a variety of routes, including oral, sublingual/buccal, rectal, vaginal, transdermal, subcutaneous, intravenous, Intravesical intramuscular and intranasal routes. The compounds of the present invention are preferably formulated prior to administration. Therefore, another embodiment of the present invention is a pharmaceutical composition or formulation comprising an effective amount of a compound of formula (1) or a pharmaceutically acceptable salt thereof and a pharmaceutically acceptable carrier, such as a diluent or excipient therefor.

The active ingredient preferably comprises from 0.1% to 99.9% by weight of the formulation. By "pharmaceutically acceptable" it is meant that the carrier, such as the diluent or excipient, is compatible with the other ingredients of the formulation and not deleterious to the host or patient.

Pharmaceutical formulations may be prepared from the compounds of the invention by known procedures using known and readily available ingredients. In making the compositions of the present invention, the active ingredient will usually be admixed with a carrier, or diluted by a carrier, or enclosed within a carrier, which may be in the form of a capsule, sachet, paper or other suitable container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments (containing, for example, up to 10% by weight of the active compound), soft and hard gelatin capsules, suppositories, sterile injectable solutions, sterile packaged powders and the like. Since the compounds of this invention are quite lipophilic, it may be necessary to solubilize them in a suitable carrier such as any one of the pharmaceutically acceptable cyclodextrin derivatives (Mitsunori and Lan, U.S. Pat. No. 6,303,157 and Amdidouche-Hussain et.al., 1997 Drug Development and Industrial Pharmacy, 23, 1223).

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention. Without further elaboration, it is believed that the above description has adequately enabled the present invention. The following specific example is, therefore, to be construed as merely illustrative, and not limitative of the remainder of the disclosure in any way whatever. All of the publications cited herein are hereby incorporated by reference in their entirety

EXAMPLE 1

Figure 5:
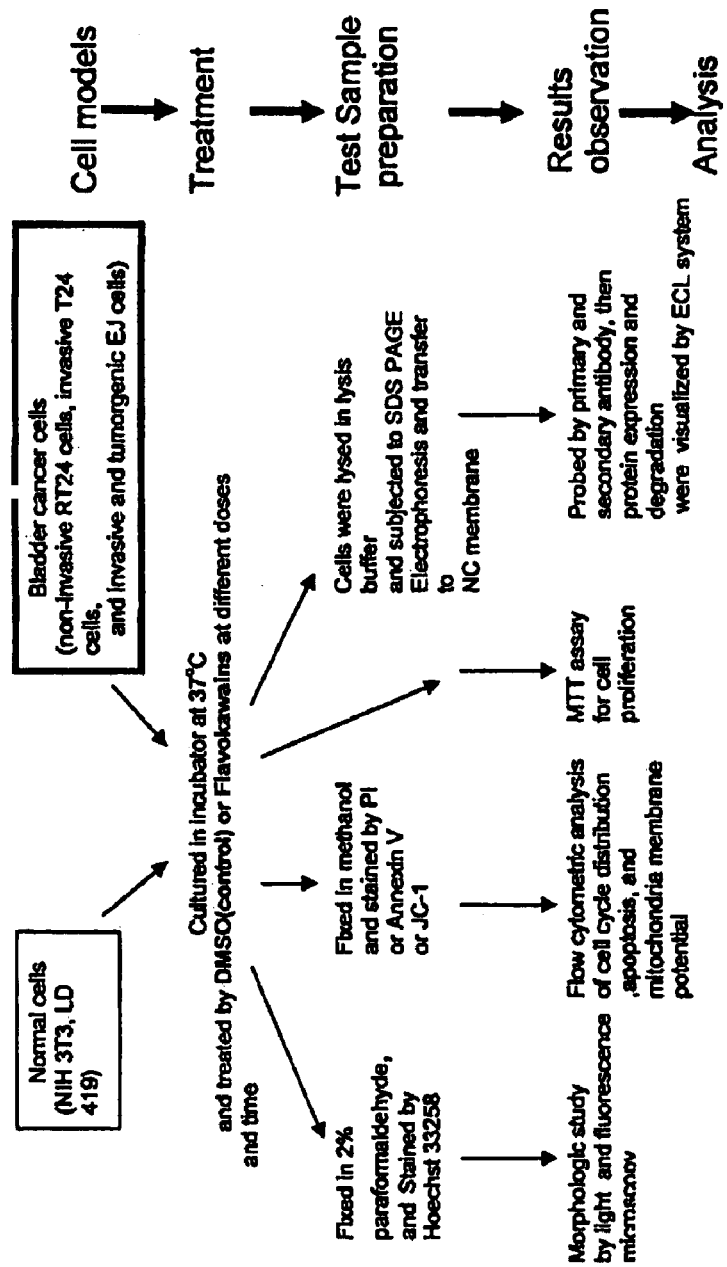
FIG. 5 is a schematic diagram of the in vitro test for antiproliferative activity referred to in Example 1 below.

Compounds of the present invention were tested for antiproliferative activity against RT24 (Grade I) and T24 (Grade3, non-metastatic) bladder cancer cells in vitro, in accordance with well known standard technique as diagramed in FIG. 5. The results of this testing are summarized in the table hereinbelow:

| Compound | Concentrations | Percentage of inhibition related to control (%) |
|---|---|---|
| Kaempferol | 50 µg/ml | 60 |
| Coumestrol | 50 µg/ml | 30 |
| Morin | 50 µg/ml | 34 |
| Naringenin | 50 µg/ml | 20 |
| Quercetin | 50 µg/ml | 53.3 |
| Naringin | 50 µg/ml | 29 |
| Taxifolin | 50 µg/ml | 36.7 |
| Cafestol Acetate | 50 µg/ml | 57.6 |
| Berberine | 50 µg/ml | 17.9 |
| Curcumin | 50 µg/ml | 69.7 |
| Rutaecurpine | 50 µg/ml | 76 |
| Resveratrol | 50 µg/ml | 70.6 |
| Ellagic acid | 100 µM | 66 |
| Procyanidin B1 | 25 µg/ml | 44.2 |
| Silibinin | 100 µM | 40 |
| EGCG | 25 µg/ml | 34 |
| Rutin | 100 µM | 47.7 |
| Biochanin A | 25 µg/ml | 48.7 |
| Kahweol | 50 µg/ml | 61.2 |
| Daidzein | 50 µg/ml | 39.3 |
| Genistein | 25 µg/ml | 48.7 |
| Kawain | 25 µg/ml | 33.6 |
| 11-Methoxyangonin | 25 µg/ml | 26.3 |
| 11-Methysticin | 25 µg/ml | 52.1 |
| 1-(2,4-Dihydorxy-6-methoxy-phenyl-3-hydorxy-3-phenyl-propan-1-one | 25 µg/ml | 42.3 |
| 4'-hydroxy-4,2',6'-trimethoxychalcone (Formula 1, Compound i) | 25 µg/ml | 73.7 |

The results show that 4'-hydroxy-4,2',6'-trimethoxychalcone (Formula 1, Compound i) of this invention is a strong inhibitor (73.7%) of the cell proliferation in $T_{24}$ bladder cancer cells.

Additionally, FIGS. 1-4 show in graphic format the effects of certain compounds of the present invention in inhibiting the growth of bladder cancer cells. In particular, 2'-hydroxy-4,4',6'-trimethoxychalcone (Flavokawain A—Compound v of Formula 1) is shown to have significant inhibitory effects on the proliferation of RT24 (Grade I) and T24 (Grade 3, non-metastatic) bladder cancer cells in vitro. In view of their structural similarities, the remaining Compounds of Formulae 1, 2, 3A, 3B, 3C, 4A and 4B are expected to also inhibit proliferation of bladder cancer cells.

Although exemplary embodiments of the invention have been shown and described, many changes, modifications and substitutions may be made by those having ordinary skill in the art without necessarily departing from the spirit and scope of this invention. For example, elements, components or attributes of one embodiment or example may be combined with or may replace elements, components or attributes of another embodiment or example to whatever extent is possible without causing the embodiment or example so modified to become unusable for its intended purpose. Accordingly, it is intended that all such additions, deletions, modifications and variations be included within the scope of the following claims. Also, although several illustrative examples of means for practicing the invention are described above, these examples are by no means exhaustive of all possible means for practicing the invention. The scope of the invention should therefore be determined with reference to the appended claims, along with the full range of equivalents to which those clams are entitled.

What is claimed is:

1. A method for treating bladder or urinary tract cancer in a human or veterinary patient, said method comprising the step of administering to the patient a therapeutically effective amount of a compound selected from the group consisting of:
   4'-hydroxy-4,2',6'-trimethoxychalcone;
   2'-hydroxy-4,4',6'-trimethoxychalcone (Flavokawain A);
   2'-4-dihydroxy-4',6'-dimethoxychalcone (Flavokawain C);
   2',4,6'-trihydroxy-4'-methoxy-3'-prenylchalcone (Xanthogalenol)
   2',6',4-trimethoxy-4'-hydroxy-3'-prenylchalcone; and pharmaceutically acceptable salts thereof.

2. A method according to claim 1 wherein the compound is administered orally.

3. A method according to claim 1, wherein the compound is administered intravesically.

4. A method according to claim 1 wherein the compound is administered at a dose of from about 0.01 mg per kilogram of body weight per day to about 100 mg/kg of body weight per day, in a single daily dose or divided into more than one daily dose.

5. A method according to claim 1 wherein the compound is administered at a dose of from about 0.05 mg per kilogram of body weight per day to about 50 mg/kg of body weight per day. In a single daily dose or divided into more than one daily dose.

6. A method according to claim 1 wherein the compound is administered at a dose of from about 0.1 mg per kilogram of body weight per day to about 25 mg/kg of body weight per day, in a single daily dose or divided into more than one daily dose.

7. A method according to claim 1 wherein the compound is administered parenterally.

8. A method according to claim 1 wherein the compound is administered in combination with at least one other compound selected from the group consisting of: cisplatin, carboplatin, taxanes, paclitaxel, docetaxel, gemcitabine, ifosfamide, methotrexate, trimetrexate, piritrexim, thiotepa, doxorubicin and mitomycin.

* * * * *